(12) United States Patent
Que et al.

(10) Patent No.: US 7,612,883 B2
(45) Date of Patent: Nov. 3, 2009

(54) DYNAMIC PLASMONICS-ENABLED SIGNAL ENHANCEMENT, A DEVICE COMPRISING THE SAME, AND A METHOD USING THE SAME

(75) Inventors: Long Que, Rexford, NY (US); Jeffrey Bernard Fortin, Niskayuna, NY (US); Christopher Fred Keimel, Schenectady, NY (US); Liming Yu, Clifton Park, NY (US); Zhiyong Wang, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 378 days.

(21) Appl. No.: 11/749,950

(22) Filed: May 17, 2007

(65) Prior Publication Data

US 2008/0285039 A1 Nov. 20, 2008

(51) Int. Cl.
*G01N 21/25* (2006.01)
(52) U.S. Cl. .................. 356/417; 356/244; 356/445
(58) Field of Classification Search .......... 356/445, 356/417, 244
See application file for complete search history.

(56) References Cited

U.S. PATENT DOCUMENTS

| | | | |
|---|---|---|---|
| 6,875,475 B2 | 4/2005 | Moran et al. | |
| 6,980,716 B1 | 12/2005 | Diaz et al. | |
| 7,060,510 B2 | 6/2006 | Bonnell et al. | |
| 2003/0215638 A1 | 11/2003 | Charnay et al. | |
| 2004/0009298 A1 | 1/2004 | Moran et al. | |
| 2005/0250243 A1 | 11/2005 | Bonnell et al. | |
| 2006/0189004 A1 | 8/2006 | Bonnell et al. | |
| 2006/0221343 A1 | 10/2006 | Bouhelier et al. | |
| 2006/0274295 A1 | 12/2006 | Brueck et al. | |
| 2006/0275541 A1 | 12/2006 | Weimer | |
| 2006/0289761 A1 | 12/2006 | Nabet et al. | |
| 2007/0086001 A1* | 4/2007 | Islam et al. | 356/301 |
| 2008/0024776 A1* | 1/2008 | Bratkovski et al. | 356/301 |

OTHER PUBLICATIONS

Lu et al., "High-density silver nanoparticle film with temperature-controllable interparticle spacing for a tunable surface enhanced Raman scattering substrate" 2005, Nano Letters, vol. 5, No. 1, pp. 5-9.*
F.I. Baida et al, Light transmission by subwavelength annular aperture arrays in metallic films, Optics Communications 209, (2002) Aug. 1, 2002, Elsevier Science B.V France.
T.W. Ebbesen et al., Extraordinary optical transmission through sub-wavelength hole arrays, Nature, vol. 391 pp. 667-669, Feb. 12, 1998.
A Degiron et al. The role of localized surface plasmon modes in the enhanced transmission of periodic subwavelength apertures, Journal of Optics A: Pure and Applied Optics, Opt 7 (2005) IOP Publishing Ltd.
M.L. Roukes, Nanoelectromechanical Systems, Technical Digest of the 2000 Solid-State Sensor and Actuator Workshop, Hilton Head Island, SC Jun. 4-8, 2000.

* cited by examiner

*Primary Examiner*—Kara E Geisel
(74) *Attorney, Agent, or Firm*—Joseph J. Christian

(57) ABSTRACT

Disclosed herein is a plasmonics platform comprising a substrate; a plurality of periodically spaced nanoholes and/or nanoparticles disposed upon the substrate; wherein the average first order of periodicity between the nanoholes and/or the nanoparticles is about 5 to about 1,000 nm; and a microelectromechanical and/or a nanoelectromechanical system in operative communication with the substrate so as to vary the average first order of periodicity between the nanoholes and/or the nanoparticles.

25 Claims, 7 Drawing Sheets

DYNAMIC PLASMONICS-ENABLED SIGNAL ENHANCEMENT, A DEVICE COMPRISING THE SAME, AND A METHOD USING THE SAME

BACKGROUND OF THE INVENTION

This disclosure relates to dynamic plasmonics-enabled signal enhancement, devices comprising the same, and methods using the same.

Fluorescence-based and surface enhanced Raman spectroscopy (SERS) are beginning to be widely used in molecular imaging and diagnostics. Techniques using fluorescence include fluorescence lifetime imaging (FLIM), where the imaging of fluorescence lifetime provides a robust means of acquiring spatially resolved information regarding the local environment of a distributed fluorophore in biological tissue and other heterogeneous or turbid media. Other techniques that use picosecond time resolution and nanometer spectral resolution are Foerster's Resonance Energy Transfer (FRET), Fluorescence Activated Cell Sorting (FACS), Fluorescence Lifetime Micro-Spectroscopy (FLMS), polarized fluorescence recovery or redistribution after photobleaching (PFRAP), or the like.

Fluorescence-based techniques generally use a light source for exciting a fluorophore in a biological molecule that is to be imaged or analyzed. The light source can be a lamp source that provides a continuous light output from 250 nanometers (nm) to 750 nm. Sets of optical devices, such as dichroic filters, prisms, or the like, are employed in such a fluorescence-based technique to select the desired excitation and emission wavelengths. Versatility is one of the advantages of such a fluorescence-based technique. The user can change the electromagnetic spectrum by changing the lamp source.

Changing the lamp source has a number of drawbacks. The fluorescence signal emitted by the molecule can be weak depending upon the lamp source used for the irradiation, as a result of which the lamp source may have to be changed to stimulate fluorescence to from an unknown specimen whose molecular imaging or structural features are desired. The sensitivity of instruments containing the lamp source is therefore not always satisfactory.

Another commonly used light source is a laser diode. Laser diodes emit strong monochromatic radiation and therefore promise higher sensitivities. Laser diodes are however, expensive to produce and are not tunable. Having a collection of lasers to probe multiple species of biomolecules with different fluorescent fluorophores is therefore practically difficult. FIG. 1 depicts a conventional fluorescence-based technique using a laser to perform molecular imaging and diagnostics. In FIG. 1, a beam of light from a light source irradiates a molecule whose structure is desired. The molecule produces a fluorescence signal that is then analyzed for the structure of the molecule. However, the fluorescence signal emitted by the molecule can be weak depending upon the light source used for the irradiation.

Poorly performing substrates have plagued surface enhanced Raman spectroscopy (SERS) as an analytical technique since its discovery in 1977 and have effectively limited its acceptance as a reliable method for chemical analysis. Despite the discovery of single molecule sensitivity for SERS in 1997 and the subsequent explosion of interest in SERS, little progress has been made toward the development of useful substrates suitable for commercial manufacturing.

Raman spectroscopy is a chemical analysis method in which monochromatic radiation interacts with molecules (i.e., analyte molecules) and wherein the radiation is shifted in frequency through a process known as scattering. The frequency shift of the scattered radiation is equal to the vibrational frequency of the bonds between atoms in the molecule. Thus, molecules with many bonds produce scattered radiation of many frequencies. Since the vibrational frequencies of most bonds are constant (and are well known), measuring the spectrum of scattered radiation allows the frequency shifts to be determined and the identity of bonds in the molecules to be deduced. The intensity of the scattered radiation is proportional to the number of analyte molecules irradiated, so a Raman spectrum may be used to measure the amount of analyte present and the frequency shifts allow the identification of the analyte. Raman scattering is an extremely inefficient process where only one in $10^8$ incident photons is Raman scattered. To be useful as a sensor, it is desirable for the scattering process to be amplified.

If the scattering process could be amplified, SERS is a vibrational spectroscopic technique that may offer higher sensitivity and versatility Historically, a number of challenges have existed that have inhibited the successful development and commercialization of SERS substrates. SERS substrates producing enhancement factors of greater than or equal to about $10^7$ for a wide range of analyte molecules do not exist and known substrates show large enhancements for an extremely limited range of highly conjugated organic molecules such as dyes.

Fabrication methods are complex multi-step laboratory processes that are not suitable for scale up to production manufacturing levels. Finally, substrate morphology on the nanoscale is difficult to reproduce and the relationship between substrate nanoscale morphology and SERS enhancement factors is poorly understood.

It is therefore desirable to have an analytical technique that is rapid, inexpensive and that can be tuned to accomplish detection, diagnosis and/or imaging in real time.

SUMMARY OF THE INVENTION

Disclosed herein is a plasmonics platform comprising a substrate; a plurality of periodically spaced nanoholes and/or nanoparticles disposed upon the substrate; wherein the average first order of periodicity between the nanoholes and/or the nanoparticles is about 5 to about 1,000 nanometers; and a microelectromechanical and/or a nanoelectromechanical system in operative communication with the substrate so as to vary the average first order of periodicity between the nanoholes and/or the nanoparticles.

Disclosed herein too is a device comprising a light source; a plasmonics platform for disposing biomolecules whose structures are desired to be known; wherein the plasmonics platform comprises a substrate; a plurality of periodically spaced nanoholes and/or nanoparticles disposed upon the substrate; wherein the average first order of periodicity between the nanoholes and/or the nanoparticles is about 5 to about 1,000 nanometers; a microelectromechanical and/or a nanoelectromechanical system in operative communication with the substrate so as to vary the average first order of periodicity between the nanoholes and/or the nanoparticles; and a detector for receiving fluorescence generated by the biomolecule.

Disclosed herein too is a method comprising disposing an unknown specimen on a plasmonics platform; wherein the plasmonics platform comprises a substrate; a plurality of periodically spaced nanoholes and/or nanoparticles disposed upon the substrate; wherein the average first order of periodicity between the nanoholes and/or the nanoparticles is about 5 to about 1,000 nanometers; a microelectromechanical and/ or a nanoelectromechanical system in operative communication with the substrate so as to vary the average first order of periodicity between the nanoholes and/or the nanoparticles; and illuminating the plasmonics platform with a source light; tuning the plasmonics platform by adjusting the average first order of periodicity between the nanoholes and/or the nanoparticles using the microelectromechanical and/or a nanoelectromechanical system; producing surface plasmon resonance in the periodically spaced nanoholes and/or the nanoparticles disposed upon the substrate; and producing fluorescence in the unknown specimen disposed upon the plasmonics platform.

DETAILED DESCRIPTION OF THE INVENTION

The use of the terms "a" and "an" and "the" and similar references in the context of describing the invention (especially in the context of the following claims) are to be construed to cover both the singular and the plural, unless otherwise indicated herein or clearly contradicted by context. The modifier "about" used in connection with a quantity is inclusive of the stated value and has the meaning dictated by the context (e.g., it includes the degree of error associated with measurement of the particular quantity). All ranges disclosed herein are inclusive of the endpoints, and the endpoints are independently combinable with each other.

Disclosed herein is a device that comprises a source of light and a tunable plasmonics platform for the detection, diagnosis and/or imaging of an unknown specimen that is disposed upon the plasmonics platform. The device further comprises a microelectromechanical system (MEMS) and/or a nanoelectromechanical system (NEMS) that enables the tuning of the plasmonics platform. The tunable plasmonics platform advantageously permits changing a periodicity between nanoholes and/or nanoparticles to affect the surface plasmon resonance of the plasmonics platform thereby enhancing the fluorescence produced by the unknown specimen. The device also comprises a detector that collects and analyses the fluorescence.

Disclosed herein too is a method comprising illuminating a plasmonics platform with a source of light. The electrons in the plasmonics platform undergo surface plasmon resonance in response to excitation by the light. The excitation of surface plasmons by the light is denoted as a surface plasmon resonance (SPR) for planar surfaces or localized surface plasmon resonance (LSPR) for nanometer-sized metallic particles or structures (hereinafter nanoparticles). The surface plasmon resonance in turn excites fluorescence in the unknown specimen. The fluorescence from the unknown specimen is then collected and analyzed by the detector to determine the structure or dynamics of the unknown specimen.

Figure 1:
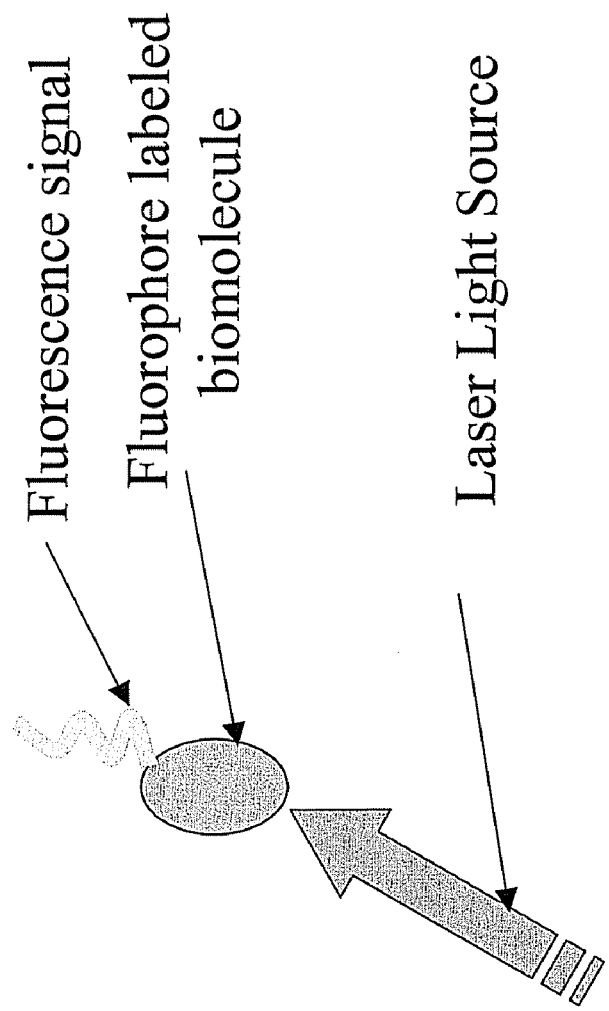
FIG. 1 depicts a conventional fluorescence-based spectroscopy technique utilizing a laser to perform molecular imaging and diagnostics.
Figure 2:
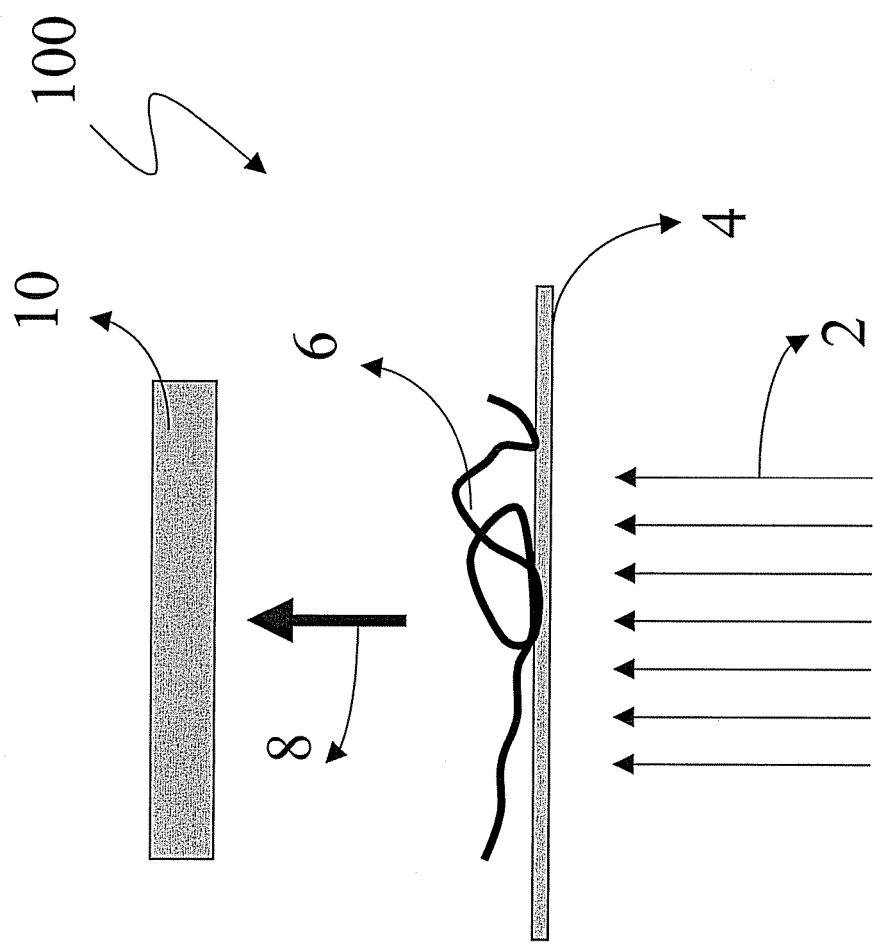
FIG. 2 illustrates a device having a source of light for illuminating a surface of a plasmonics platform.

With reference now to the FIG. 2, a device 100 is shown with a source of light 20 that illuminates a surface 23 of the plasmonics platform 24 that is opposed to the surface 22 upon which the specimen 16 is disposed. In other words, the unknown specimen 16 is disposed upon a first surface 22 of the plasmonics platform 24, while the source of light 20 irradiates a second surface 23 of the plasmonics platform 24. The second surface 23 is opposed to the first surface 22 of the plasmonics platform 24.

Figure 3:
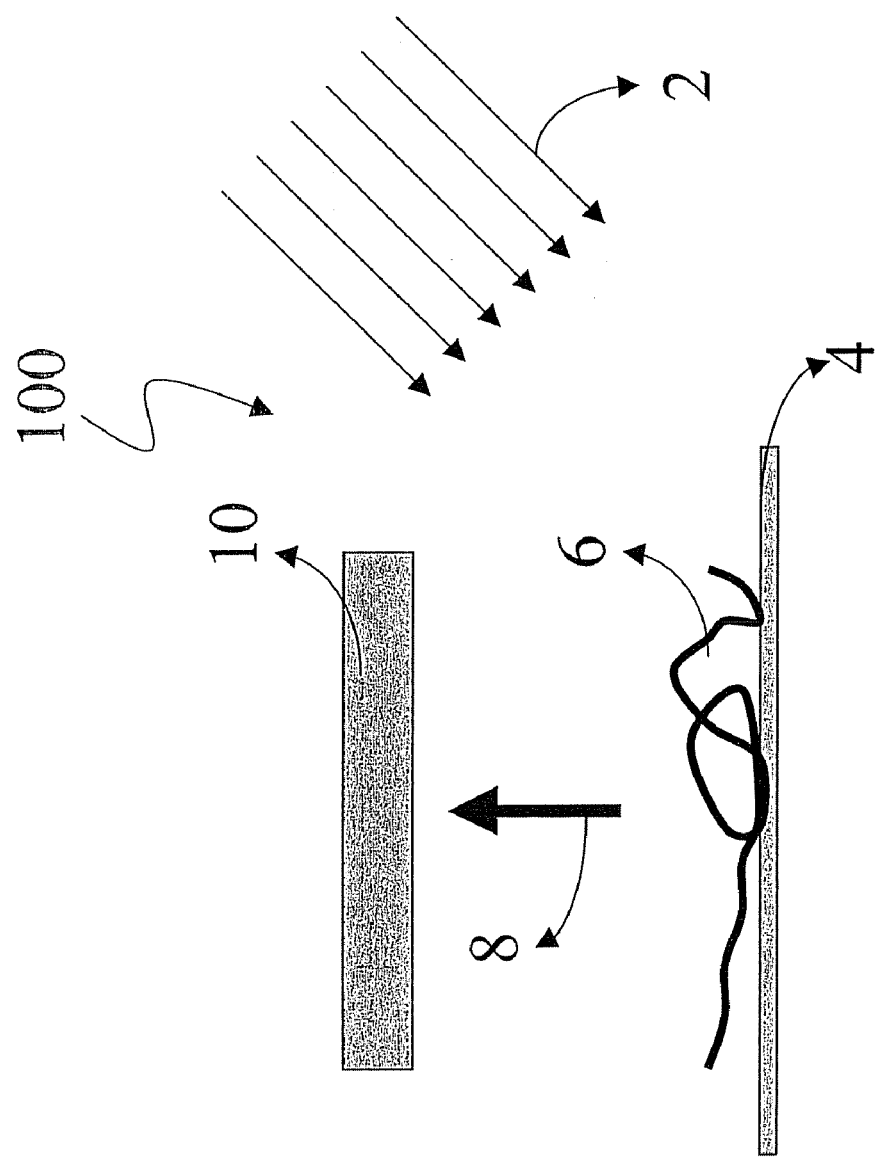
FIG. 3 illustrates a device having a source of light for illuminating a surface of a plasmonics platform.
Figure 4:
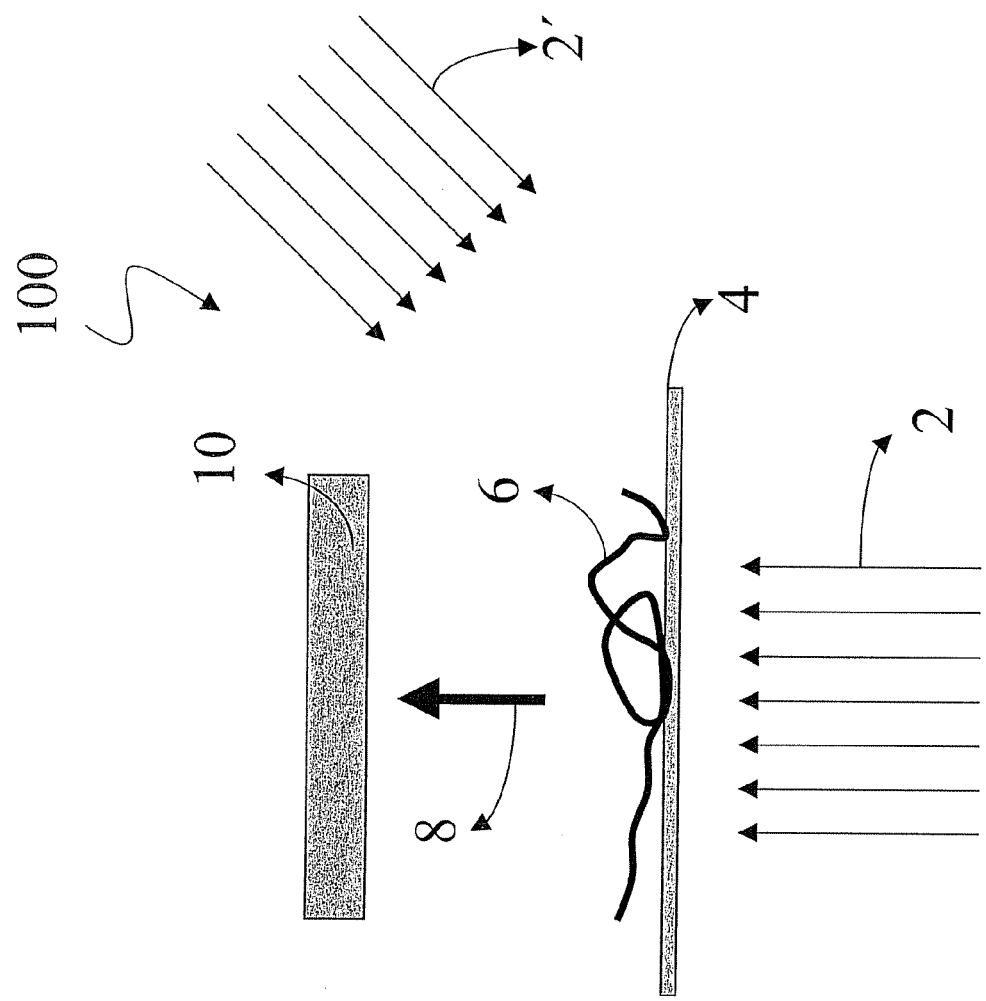
FIG. 4 illustrates a device having a plurality of sources of light for illuminating surfaces of a plasmonics platform.

In another exemplary embodiment depicted in the FIG. 3, the device 100 comprises a source of light 20 that illuminates a surface of the plasmonics platform 24 upon which the specimen 16 is disposed. In other words, the unknown specimen 16 is disposed upon a first surface 22 of the plasmonics platform 24, while the source of light 20 irradiates the first surface 22 of the plasmonics platform 24. In yet another embodiment depicted in the FIG. 4, the device 100 comprises a plurality of sources of light 20 and 20' that illuminate a surface 22 of the plasmonics platform 24 upon which the specimen 16 is disposed, as well as the surface 23 of the plasmonics platform 24 that is opposed to the surface 22 upon which the specimen 16 is disposed. As can be seen in the FIGS. 2-4, the fluorescence 18 produced by unknown specimen is collected by the detector 10.

The source of the light 20 used in the device 100 may be a broadband source of light that emits light of the electromagnetic spectrum at wavelengths from deep UV to infrared (IR) range. The broadband source of light generally comprises a high intensity light source, such as, for example, a gas discharge lamp, a gas arced pulsed lamp, an incandescent lamp, a light emitting diode (LED), or the like, or a combination comprising at least one of the foregoing, to excite surface plasmon resonance in the plasmonics platform 24. In one embodiment, a laser can be used as the light source.

Examples of gas discharge lamps are mercury lamps, sodium vapor lamps, xenon lamps, mercury-xenon lamps, or the like, or a combination comprising at least one of the foregoing gas discharge lamps.

The plasmonics platform 24 comprises a substrate upon which is disposed periodically spaced nanoparticles and/or a nanohole array. Upon irradiating the periodically spaced nanoparticles or the nanohole array with light from the light source 20, optical absorption and scattering by the nanoparticles result from the collective coherent oscillation of surface electrons, known as surface plasmons, which are excited by the incident electromagnetic radiation. When the plasmonics platform 24 comprises metal nano-particles or nanoholes in the nanoscale dimension range, surface plasmon resonance could occur at wavelengths in the ultraviolet, visible, or near infrared regions of the electromagnetic spectrum. Greatly enhanced optical absorption and scattering occurs at these surface plasmon resonance wavelengths. The nanoscale dimensional range is generally up to about 1,000 nm.

The surface plasmon resonance can improve the fluorescence from the unknown specimen disposed upon the surface of the plasmonics platform 24. Surface plasmons can help overcome the diffraction limits of size and performance in current photonic components built based on the classical electromagnetic theory. For example, surface plasmon effects can allow sub-wavelength arrays of holes in a metal film to transmit light with extraordinary transmission efficiency and act as spectral filters. At certain wavelengths, the transmission is enhanced and can be several times the combined area of the holes. Thus, the periodically spaced nanoparticles and/or nanohole array facilitates the focusing and manipulation of the incident light at spatial dimensions far below the classical diffraction limit.

In one embodiment, the tunable plasmonics platform 24 comprises a substrate upon which is disposed a film that comprises a nanohole array. In another embodiment, the tunable plasmonics platform comprises a substrate upon which are disposed nanoparticles having an average periodicity between the nanoparticles. In yet another embodiment, the tunable plasmonics platform comprises a substrate upon which is disposed a film that comprises a nanohole array as well as periodically spaced nanoparticles.

Figure 5:
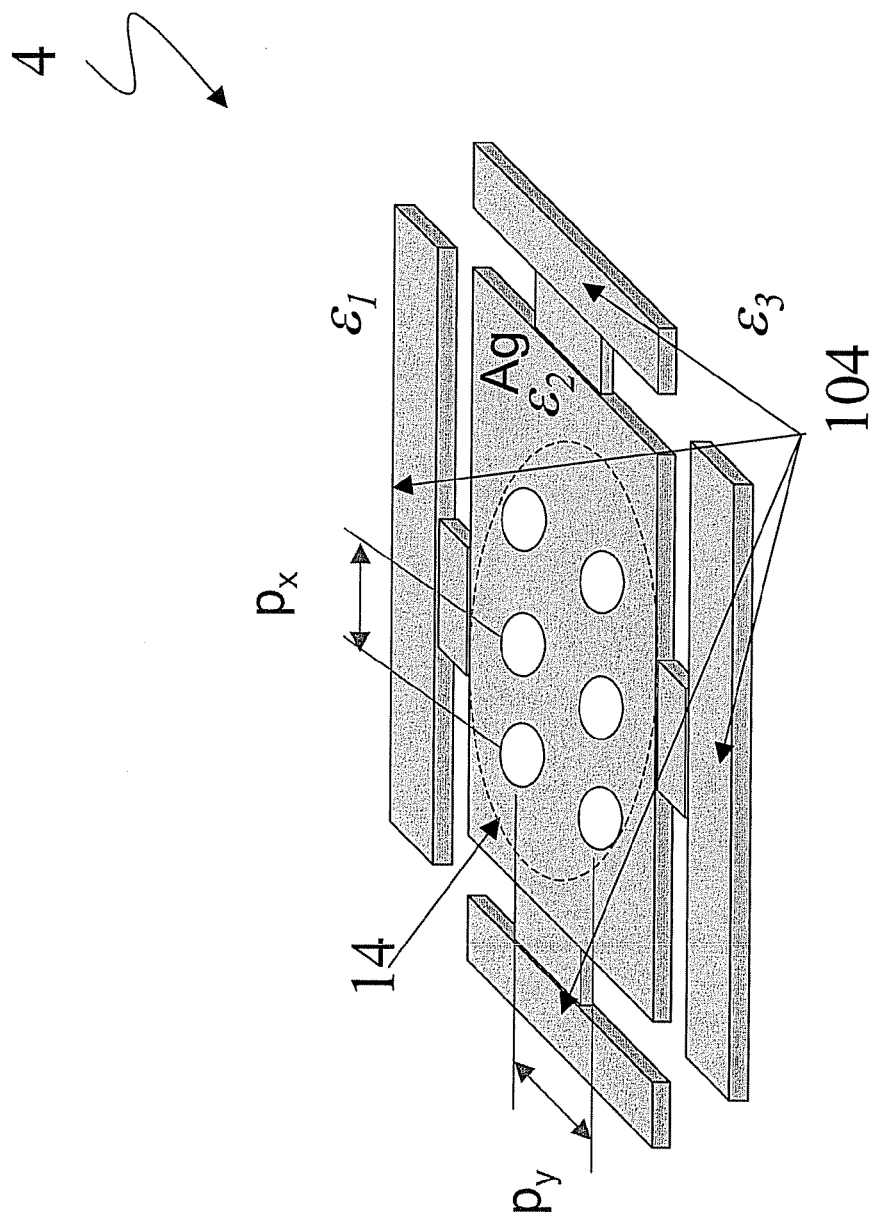
FIG. 5 illustrates a plasmonics platform in operational communication with a MEMS and/or a NEMS actuator.

FIG. 5 illustrates an embodiment of a plasmonics platform 124 in operational communication with a MEMS and/or a NEMS actuator 112. As can be seen in the FIG. 5, the plasmonics platform 124 comprises a nanohole array 114 having periodic dimensions $p_x$ and $p_y$, respectively, between the nanoholes in the nanohole array.

By varying the periodic dimensions $p_x$ and $p_y$ by activating the MEMS or NEMS actuator 112, the transmission maxima wavelength $\lambda_{max}$ is varied. The transmission maxima wavelength $\lambda_{max}$ is represented by the Equation (I) below:

$$\lambda_{max}(i, j) = \frac{p_x p_y}{\sqrt{i^2 p_y^2 + j^2 p_x^2}} \sqrt{\frac{\varepsilon_{1,3} \varepsilon_2}{\varepsilon_{1,3} + \varepsilon_2}} \qquad (I)$$

where $\epsilon_1$, $\epsilon_2$, and $\epsilon_3$ are the permittivities for the incident medium, the metal film and the transmission medium (i.e., the substrate) and i and j are integers.

The substrate can be manufactured from a variety of different materials such as quartz, silicon, ferroelectric materials, or the like. In one embodiment, the substrate can comprise ferroelectric materials. The ferroelectric substrate may be inorganic, e.g., a ferroelectric ceramic material, or organic, e.g., a ferroelectric polymer, and may be grown on a semiconductor substrate, such as silicon. A ferroelectric material is one that contains electrical dipoles having a local surface charge associated therewith. The electric polarization of a ferroelectric material can be oriented by application of an external energy field, such as an electric field. Other processes that could be used to pattern the surface charge include exposure to optical illumination or an electron beam through a mask, exposure to interference patterns of two or more optical or electron beams, and application of electric fields from patterned electrodes (for example those produced from microcontact printing). Representative examples of ferroelectric materials include barium titanate, lead titanate, lead zirconate titanate (PZT), tri-glycine sulfate (TGS), guanidinium aluminum sulfate hexahydrate (GASH), or the like, or a combination comprising at least one of the foregoing ferroelectric materials. The ferroelectric material may be in the form of a thin film, a thick polycrystalline film, or a single crystal.

When the plasmonics platform comprises a nanohole array, it is desirable that a metal film be first disposed upon the substrate. The metal film may be disposed upon the substrate by a variety of methods. Exemplary methods are electroless plating, expanding thermal plasma (ETP), ion plating, plasma enhanced chemical vapor deposition (PECVD), metal organic chemical vapor deposition (MOCVD) (also called Organometallic Chemical Vapor Deposition (OMCVD)), metal organic vapor phase epitaxy (MOVPE), physical vapor deposition processes such as sputtering, reactive electron beam (e-beam) deposition, and plasma spray.

Examples of metals that may be used in the metal film are gold, silver, platinum, palladium, lead, iron, nickel, copper, titanium, chromium, or the like, or a combination comprising at least one of the foregoing metals.

The metal film is then perforated with a periodic array of subwavelength nanoholes. In order to develop a nanohole array, various techniques that involve the use of masking, pre-patterning, passivation, nanolithography, or the like, may be used on the substrate. Exemplary methods for developing periodic arrays of subwavelength nanoholes and/or nanoparticles are described in U.S. Pat. No. 6,875,475 to Moran et al., U.S. Pat. No. 7,060,510 to Bonnell et al., U.S. Patent Application No. 2003/0215638 to Charnay et al., and U.S. Patent Application No. 2006/0274295 to Brueck et al., the entire contents of which are hereby incorporated by reference. In one embodiment, the periodic nanohole array is fabricated using a focused ion beam (FIB).

The nanoholes may have any desired cross-sectional geometry. The cross-sectional geometry of the individual nanoholes may be triangular, square, circular, rectangular, polygonal, or a combination comprising at least one of the foregoing geometries. In addition, the cross-sectional area of the nanoholes may be varied along the thickness of the metal film.

As noted above, the plasmonics platform also may contain nanoparticles. The nanoparticles may be disposed upon the substrate using the same deposition techniques described above for depositing the metal film. Techniques involving the use of masking, pre-patterning, passivation, nanolithography, or the like, also may be used to deposit and build nanoparticles on the substrate. If nanoparticles are disposed upon the substrate in lieu of nanoholes, the nanoparticle agglomerates can have a regular or irregular shape. A regular shape is one that follows the laws of Euclidean geometry. An example of a nanoparticle agglomerate that has a regular two-dimensional shape is a square, a triangle, a circle, a rectangle, a polygon, or the like, or a combination comprising at least one of the foregoing two-dimensional shapes. An example of a nanoparticle agglomerate that has a regular three-dimensional shape is a cuboid, a pyramid, a sphere, a hemisphere, a fullerene, or the like, or a combination comprising at least one of the foregoing three-dimensional shapes.

An irregular shape is one that does not obey the laws of Euclidean geometry. Exemplary irregular shapes are fractals or those shapes whose surfaces can be defined by polynomial equations. The nanoparticles can be surface or mass fractals. Irregular shapes also include non-symmetrical geometries.

The metal film generally has a thickness of about 5 to about 1,000 nm. A preferred thickness for the metal film is about 200 nanometers. The average first order periodicity between the nanoholes or nanoparticles is about 5 to about 1,000 nm, specifically about 5 to about 120 nm, specifically about 10 to about 100 nm, more specifically about 20 to about 80 nm, and even more specifically about 30 to about 70 nm.

As noted above, the periodicity between the nanoholes or nanoparticles can be advantageously manipulated using a microelectromechanical system (MEMS) and/or a nanoelectromechanical system (NEMS). In the micrometer and the sub-micrometer (nanometer) size regime, it is possible to attain high fundamental frequencies while simultaneously preserving high mechanical responsivity.

The MEMS or NEMS actuator 112 can be in thermal, mechanical, fluid, electrical, magnetic or electromagnetic communication with the plasmonics platform 124. As noted above, the actuator 112 can be activated to change the periodicity of the nanohole arrays or the periodicity of nanoparticles. In an exemplary embodiment, the actuator 112 comprises a piezoelectric crystal to which an electric current can be applied. Applying the electric current causes a change in the dimensions of the piezoelectric crystals, which facilitates a change in the periodicity of the nanohole arrays or the periodicity of nanoparticles.

In another exemplary embodiment, the actuator 112 comprises a shape memory alloy to that changes its dimensions upon changing the temperature. By changing the temperature, the shape memory alloy changes it dimensions, which facilitates a change in the periodicity of the nanohole arrays or the periodicity of nanoparticles.

Figure 6:
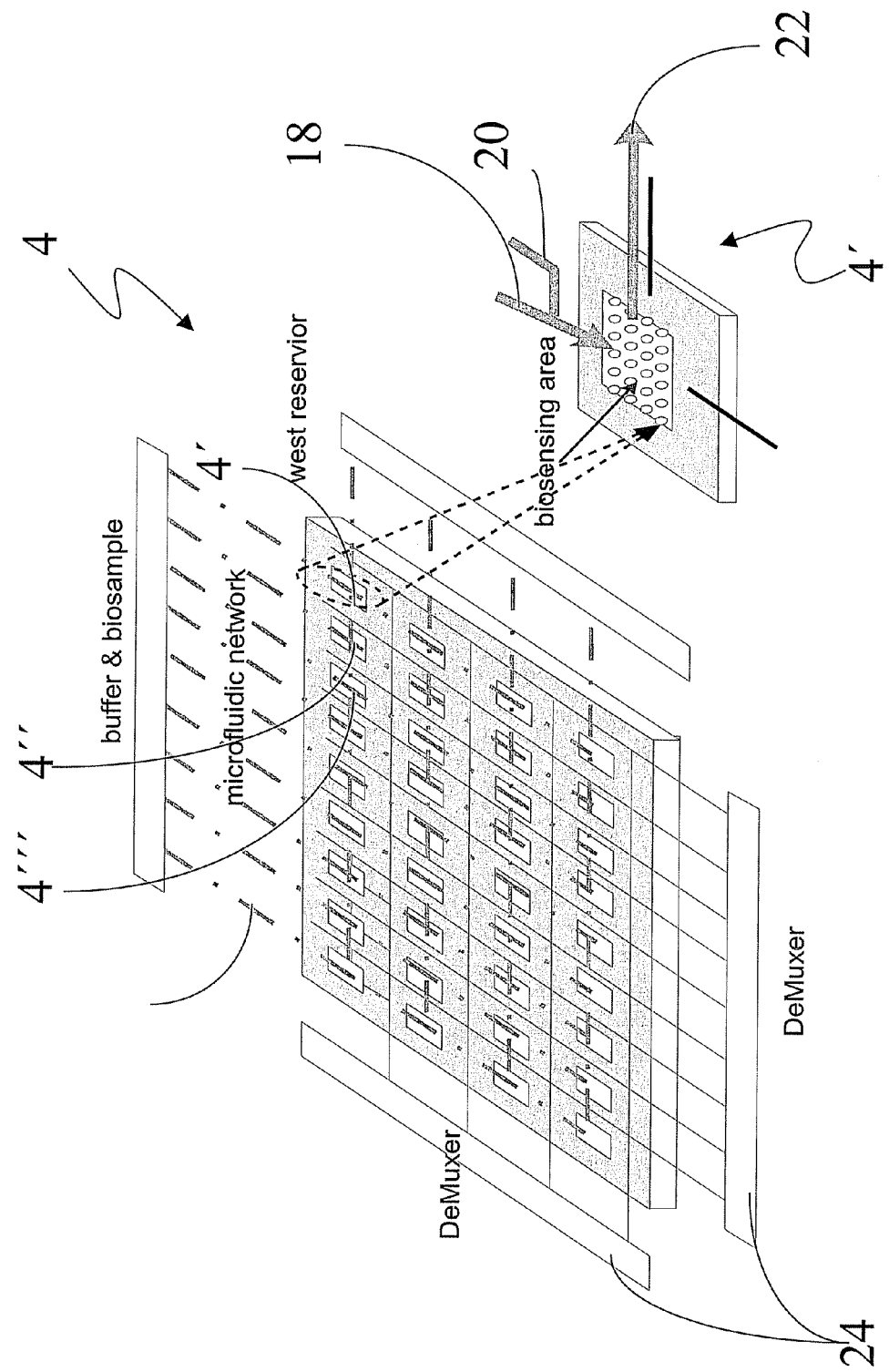
FIG. 6 illustrates a plasmonics platform having a plurality of plasmonics platforms.

With reference now to the FIG. 6, a plasmonics platform 224 may comprise a plurality of plasmonics platforms 224', 224", 224''', and the like. Each of the plurality of plasmonics platforms is in fluid communication with a microfluidic device 216 that can supply the unknown specimen along with a buffer and other reactants to the respective plasmonics platform. As shown in the enlarged portion of the plasmonics platform 224', the microfluidics device provides a first microchannel 218 for the introduction of the unknown specimen (e.g., biomaterials) onto the plasmonics platform 224', a second microchannel 220 for the introduction of the buffer onto the plasmonics platform 224', a third microchannel 222 for removing spent biomaterials to a waste reservoir. Additional microchannels may be provided for other purposes. The MEMS or NEMS actuator (not shown) can cause a variation in the periodicity of the nanohole array or the periodicity of the nanoparticle array for each plasmonics platform.

Each plasmonics platform is also provided with a digital video disk (DVD) Demuxer 226 which provides for a real time decompilation of all data streams. The use of a plurality of plasmonics platforms as shown in the FIG. 6 permits the rapid sampling as well as the analysis and/or imaging of a variety of unknown specimens.

The plasmonics platform can also be in communication with a controlling device (not shown) such as, for example, a computer or a microprocessor. The controlling device can determine the amount of change in the periodicity in the nanohole array and the periodicity of the nanoparticles, can determine the amount of fluids used for transferring the unknown specimen to the plasmonics platform, and compile and analyze the amount fluorescence received from the unknown specimen.

Figure 7:
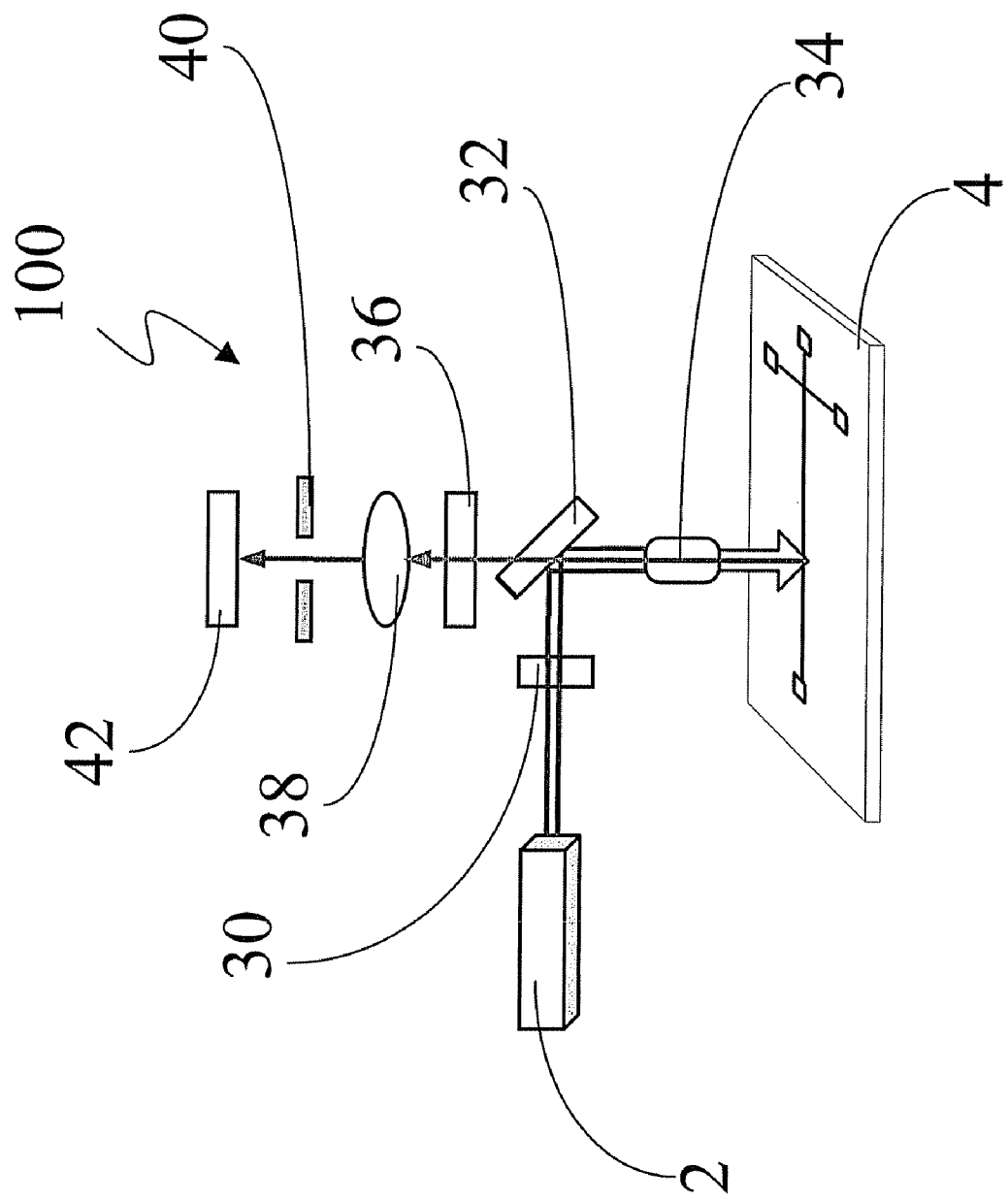
FIG. 7 illustrates a device for analyzing the structure of unknown biomaterials.

In one embodiment, in one manner of proceeding, a device 300 is shown in FIG. 7 for analyzing the structure of unknown biomaterials comprises a light source 20 that directs the light via a bandpass filter 30, a dichroic mirror 32 and a microscope objective 34 to a plasmonics platform 24. In an exemplary embodiment, the light source 20 is a laser light source. As noted above, the plasmonics platform 4 is tuned via a MEMS/NEMS actuator (not shown) so as to obtain an effective fluorescence signal from the unknown biomaterial. The fluorescence signal is acquired and counted in a photomultiplier tuber (PMT) 42, via a high pass filter 36, a lens 38 and a slit 40.

The device detailed above has a number of applications. For example, it can be used for automated sequencing of DNA by the chain termination method. Each of four different chain-terminating bases has its own specific fluorescent tag. As the labeled DNA molecules are separated, the fluorescent label is excited by a UV source, and the identity of the base terminating the molecule is identified by the wavelength of the emitted light.

It can also be used for DNA detection. For example, the compound ethidium bromide, when free to change its conformation in solution, has very little fluorescence. Ethidium bromide's fluorescence is enhanced when it binds to DNA, so this compound is very useful in visualising the location of DNA fragments in agarose gel electrophoresis.

Fluorescence can therefore be used to study the structure and conformations of DNA and proteins with techniques such as fluorescence resonance energy transfer (FRET). This is useful when determining the structure of complexes of multiple biomolecules.

The technique is useful for the detection of biological molecules. Many biological molecules have an intrinsic fluorescence that can sometimes be used without the need to attach a chemical tag. Sometimes this intrinsic fluorescence changes when the molecule is in a specific environment, so the distribution or binding of the molecule can be measured. Bilirubin, for instance, is highly fluorescent when bound to a specific site on serum albumin. Zinc protoporphyrin, formed in developing red blood cells instead of hemoglobin when iron is unavailable or lead is present, has a bright fluorescence and can be used to detect these problems.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A plasmonics platform, comprising:
   a substrate;
   a plurality of periodically spaced nanoholes and/or nanoparticles disposed upon the substrate, wherein an average first order of periodicity between the nanoholes and/or the nanoparticles is about 5 to about 1,000 nanometers; and
   a microelectromechanical and/or a nanoelectromechanical system in operative communication with the substrate for varying the average first order of periodicity between the nanoholes and/or the nanoparticles.

2. The platform of claim 1, wherein the substrate comprises a ferroelectric material.

3. The platform of claim 1, wherein the substrate comprises a ferroelectric ceramic material.

4. The platform of claim 2, wherein the ferroelectric material comprises barium titanate, lead titanate, lead zirconate titanate, tri-glycine sulfate, guanidinium aluminum sulfate hexahydrate, or a combination comprising at least one of the foregoing ferroelectric materials.

5. The platform of claim 1, wherein the substrate comprises a thin film, a thick polycrystalline film, or a single crystal.

6. The platform of claim 1, wherein the substrate comprises a metal oxide.

7. The platform of claim 6, wherein the metal oxide is silicon dioxide, aluminum oxide, titanium oxide, zirconium oxide, cerium oxide, or a combination comprising at least one of the foregoing metal oxides.

8. The platform of claim 1, wherein the substrate comprises quartz.

9. The platform of claim 1, wherein the substrate comprises a metal film disposed upon the substrate.

10. The platform of claim 8, wherein the metal film comprises gold, silver, platinum, palladium, lead, iron, nickel, copper, titanium, chromium, or a combination comprising at least one of the foregoing metals.

11. The platform of claim 8, wherein the metal film comprises gold or silver.

12. The platform of claim 1, wherein the nanoholes can have a cross-sectional area that is triangular, square, circular, rectangular, polygonal, or a combination comprising at least one of the foregoing geometries.

13. The platform of claim 1, wherein the nanoparticles have a regular two-dimensional shape, wherein the two-dimensional shape is a square, a triangle, a circle, a rectangle, a polygon, or a combination comprising at least one of the foregoing two-dimensional shapes; or wherein the nanoparticles have a regular three-dimensional shape that is cuboid, pyramidal, a spherical, a hemispherical, fullerene, or a combination comprising at least one of the foregoing three-dimensional shapes.

14. The platform of claim 1, wherein the microelectromechanical system and/or the nanoelectromechanical system is in thermal, mechanical, fluid, electrical, magnetic or electromagnetic communication with the plasmonics platform.

15. The platform of claim 14, wherein the microelectromechanical system and/or the nanoelectromechanical system comprises a piezoelectric crystal, and wherein an application of an electrical current to the piezoelectric crystal facilitates a change in the periodicity of the nanohole arrays or the periodicity of nanoparticles.

16. A device, comprising:
a light source;
a plasmonics platform for receiving biomolecules whose structures are desired to be known, wherein the plasmonics platform comprises:
a substrate;
a plurality of periodically spaced nanoholes and/or nanoparticles disposed upon the substrate, wherein an average first order of periodicity between the nanoholes and/or the nanoparticles is about 5 to about 1,000 nanometers; and
a microelectromechanical and/or a nanoelectromechanical system in operative communication with the substrate for varying the average first order of periodicity between the nanoholes and/or the nanoparticles; and
a detector for receiving fluorescence generated by the biomolecules.

17. The device of claim 16, wherein the light source is a broadband source of light.

18. The device of claim 16, wherein the light source is a gas discharge lamp, a gas arced pulsed lamp, an incandescent lamp, a light emitting diode, a laser diode, or a combination comprising at least one of the foregoing light sources.

19. The device of claim 18, wherein the gas discharge lamps are mercury lamps, sodium vapor lamps, xenon lamps, mercury-xenon lamps, or a combination comprising at least one of the foregoing gas discharge lamps.

20. The device of claim 16, wherein the microelectromechanical system and/or the nanoelectromechanical system is in thermal, mechanical, fluid, electrical, magnetic or electromagnetic communication with the plasmonics platform.

21. The device of claim 16, comprising a band pass filter and/or a high pass filter.

22. The device of claim 16, wherein the detector comprises a photomultiplier tube.

23. The device of claim 16, wherein the plasmonics platform comprises a plurality of plasmonics platforms each one of which is in communication with a microfluidics device, and a digital video disk Demuxer.

24. A method, comprising:
disposing an unknown specimen on a plasmonics platform, wherein the plasmonics platform comprises:
a substrate;
a plurality of periodically spaced nanoholes and/or nanoparticles disposed upon the substrate; wherein an average first order of periodicity between the nanoholes and/or the nanoparticles is about 5 to about 1,000 nanometers; and
a microelectromechanical and/or a nanoelectromechanical system in operative communication with the substrate for varying the average first order of periodicity between the nanoholes and/or the nanoparticles;
illuminating the plasmonics platform with a source light;
tuning the plasmonics platform by adjusting the average first order of periodicity between the nanoholes and/or the nanoparticles using the microelectromechanical and/or a nano electromechanical system;
producing surface plasmon resonance in the periodically spaced nanoholes and/or the nanoparticles disposed upon the substrate; and
producing fluorescence in the unknown specimen disposed upon the plasmonics platform.

25. The method of claim 24, comprising receiving the fluorescence in a detector.

* * * * *